US007514459B2

(12) United States Patent
Collins et al.

(10) Patent No.: US 7,514,459 B2
(45) Date of Patent: Apr. 7, 2009

(54) GAMMA-SECRETASE INHIBITORS

(75) Inventors: Ian James Collins, Redhill (GB); Joanne Clare Hannam, Stansted (GB); Andrew Madin, Sawbridgeworth (GB); Mark Peter Ridgill, Watton-at-Stone (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 566 days.

(21) Appl. No.: 10/571,717

(22) PCT Filed: Sep. 16, 2004

(86) PCT No.: PCT/GB2004/003973

§ 371 (c)(1), (2), (4) Date: Mar. 9, 2006

(87) PCT Pub. No.: WO2005/030731

PCT Pub. Date: Apr. 7, 2005

(65) Prior Publication Data

US 2006/0293373 A1 Dec. 28, 2006

(30) Foreign Application Priority Data

Sep. 24, 2003 (GB) ................................ 0322340.1
Sep. 24, 2003 (GB) ................................ 0322341.9

(51) Int. Cl.
*A61K 31/4164* (2006.01)
*A61K 31/4196* (2006.01)
*C07D 233/54* (2006.01)
*C07D 249/08* (2006.01)

(52) U.S. Cl. ....................... 514/361; 548/125; 548/127; 548/267.2; 548/300.1; 548/312.4; 514/383; 514/385; 514/396; 514/399

(58) Field of Classification Search ................. 548/125, 548/127, 300.1, 311.1, 312.4, 262.2, 267.2; 514/361, 383, 385, 396, 399
See application file for complete search history.

(56) References Cited

U.S. PATENT DOCUMENTS

| | | | | |
|---|---|---|---|---|
| 4,341,904 A | 7/1982 | Belanger et al. | | |
| 7,041,689 B2 * | 5/2006 | Collins et al. | ............... | 514/362 |
| 7,138,400 B2 * | 11/2006 | Collins et al. | ............ | 514/234.2 |
| 7,144,910 B2 * | 12/2006 | Madin et al. | ................ | 514/406 |
| 7,183,303 B2 * | 2/2007 | Castro Pineiro et al. | ..... | 514/372 |
| 7,282,513 B2 * | 10/2007 | Collins et al. | ............... | 514/362 |

FOREIGN PATENT DOCUMENTS

| | | |
|---|---|---|
| EP | 0 020 885 | 1/1981 |
| WO | WO 98/38156 | 9/1998 |
| WO | WO 01/70677 | 9/2001 |
| WO | WO 02/36555 | 5/2002 |
| WO | WO 03/013506 | 2/2003 |
| WO | WO 03/093251 | 11/2003 |
| WO | WO 03/093252 | 11/2003 |
| WO | WO 03/093253 | 11/2003 |
| WO | WO 03/093264 | 11/2003 |
| WO | WO 2004/039370 | 5/2004 |
| WO | WO 2004/039800 | 5/2004 |

OTHER PUBLICATIONS

P. C. Belanger et al., "Synthesis and Stereochemistry of 11-Substituted 5,6,7,8,9,10-Hexahydro-6,9-methanobenzocyclooctenes," J. Org. Chem., vol. 47, pp. 4329-4334 (1982).
J. E. Franz, et al.: Journal of Organic Chemistry, vol. 29, No. 10, Oct. 1964, pp. 2922-2927.
R. Huisgen, et al.: Chemische Berichte, vol. 98, No. 12, Dec. 1965, pp. 3992-4013.
S. Itsuno, et al.: Journal of the Chemical Society, Perkin Transactions 1, No. 10, Jul. 15, 1999, pp. 2011-2016.
K. B. Sharpless, et al.: Journal of Organic Chemistry, vol. 41, No. 1, Jan. 9, 1976, pp. 176-177.
Y. Yamaguchi, et al.: Xenobiotica, vol. 26, No. 6, Jun. 1996, pp. 613-626.
L. H. Zalkow, et al.: Journal of the American Chemical Society, vo. 86, No. 19, pp. 4208-4209, Oct. 5, 1964.
L. H. Zalkow, et al.: Journal of Organic Chemistry, vol. 28, No. 12, Dec. 1963, pp. 3303-3309.
J. L. Castro et al., "Synthesis and Biological Activity of . . . ," J. Med. Chem., vol. 37(19), pp. 3023-3032, (1994).
P. Aeberli et al., "Neuropharmacological Investigation of N-Benzylsulfamides," J. Med. Chem., vol. 10(4), pp. 636-642, (1967).
A. C. Oehlshlager et al., "Bridged Ring Compounds . . . ," J. Org. Chem., vol. 31, pp. 1682-1688, (1965).
G. M. Rishton et al., "Fenchylamine Sulfonamide Inhibitors of Amyloid Beta Peptide Production by the Gamma-Secretase Proteolytic Pathway . . . ", J. Med. Chem, vol. 43, pp. 2297-2299 (2000).
M. Narisada et al.: Journal of Medicinal Chemistry, vol. 31, No. 9, Sep. 1988, pp. 1847-1854.

* cited by examiner

*Primary Examiner*—Golam M Shameem
(74) *Attorney, Agent, or Firm*—William Krovatin; Raynard Yuro

(57) ABSTRACT

Compounds of formula I:

I

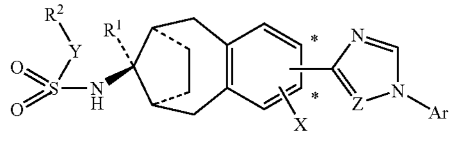

are potent inhibitors of gamma-secretase and hence find use in treatment or prevention of diseases associated with deposition of β-amyloid.

12 Claims, No Drawings

GAMMA-SECRETASE INHIBITORS

CROSS REFERENCE TO RELATED APPLICATIONS

This application is a U.S. National Phase application under 35 U.S.C. § 371 of PCT Application No. PCT/GB2004/003973, filed Sep. 16, 2004, and claims priority under 35 U.S.C. § 119 from GB Application No. 0322340.1, filed Sep. 24, 2003 and GB Application No. 0322341.9, filed Sep. 24, 2003.

The present invention relates to a novel class of compounds, their salts, pharmaceutical compositions comprising them, processes for making them and their use in therapy of the human body. In particular, the invention relates to novel sulphonamide, sulphamate and sulphamide derivatives which inhibit the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are various reports in the literature of compounds with inhibitory activity towards γ-secretase, as measured in cell-based assays. These are reviewed in WO 01/70677. Many of the relevant compounds are peptides or peptide derivatives.

WO 01/70677 and WO 02/36555 disclose, respectively, sulphonamido- and sulphamido-substituted bridged bicycloalkyl derivatives which are believed to be useful in the treatment of Alzheimer's disease, but do not disclose or suggest compounds in accordance with the present invention.

The present invention provides a novel class of bridged bicycloalkyl sulphonamide, sulphamate and sulphamide derivatives which show a particularly strong inhibition of the processing of APP by the putative γ-secretase, and thus are useful in the treatment or prevention of AD.

According to the invention there is provided a compound of formula I:

I

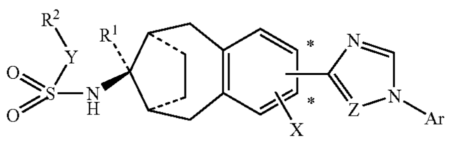

wherein Z represents CH or N and the resulting imidazole or triazole group is attached at one of the positions indicated by an asterisk and X is attached at a position adjacent thereto;

X represents H, OH, $C_{1-4}$alkoxy, Cl or F;

Y represents a bond, O or $NR^3$;

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

$R^1$ represents H; or when Y represents $NR^3$, $R^1$ and $R^3$ may togeher represent —$CH_2$—;

$R^2$ represents H or a hydrocarbon group of 1-10 carbon atoms which is optionally substituted with CN, $C_{1-4}$alkoxy or up to 3 halogen atoms; or $R^2$ represents heteroaryl of 5 or 6 ring atoms optionally bearing up to 3 substituents independently selected from halogen, $CF_3$, $CHF_2$, $CH_2F$, $NO_2$, CN, $OCF_3$, $C_{1-6}$alkyl and $C_{1-6}$alkoxy; or when Y represents $NR^3$, $R^2$ and $R^3$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy; and $R^3$ represents H or $C_{1-4}$alkyl, or together with $R^2$ completes a heterocyclic ring as defined above; or togeher with $R^1$ represents —$CH_2$—;

provided that when X is H, and Y represents $NR^3$ and $R^1$ and $R^3$ together represent —$CH_2$—, $R^2$ does not represent 2,2,2-trifluoroethyl; and provided that $R^1$ and $R^2$ are not both H;

or a pharmaceutically acceptable salt thereof.

It will be readily apparent to those skilled in the art that any compound in accordance with formula I may exist in two enantiomeric forms, depending on which of the ring positions indicated by an asterisk is bonded to the imidazole or triazole ring. Formula I thus encompasses enantiomers of formulae IIa and IIb:

IIa

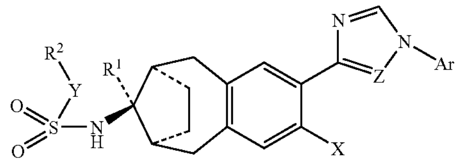

IIb

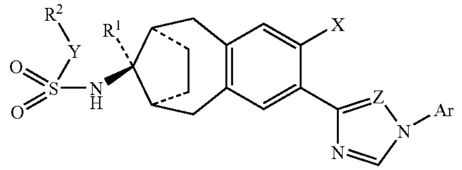

wherein X, Y, Z, Ar, $R^1$ and $R^2$ are as defined previously;

and also enantiomers of formulae IIIa and IIIb:

IIIa

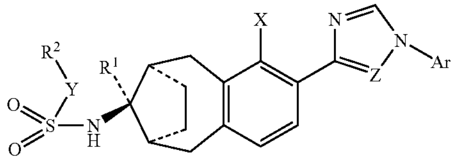

-continued

IIIb

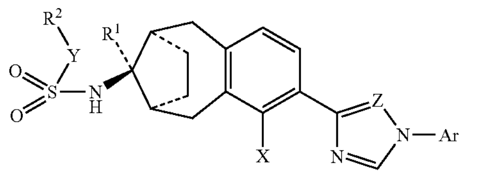

wherein X, Y, Z, Ar, $R^1$ and $R^2$ are as defined previously.

It will also be apparent that when X represents H formula IIa is identical to formula IIIa and formula IIb is identical to formula IIIb.

It is to be emphasised that the invention, for each compound in accordance with formula I, encompasses both enantiomeric forms, either as homochiral compounds or as mixtures of enantiomers in any proportion.

In a preferred embodiment of the invention, the compound of formula I is a homochiral compound of formula IIa or formula IIIa, or a pharmaceutically acceptable salt thereof, or a racemic mixture comprising a compound of formula IIa or formula IIIa, or a pharmaceutically acceptable salt thereof.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The expression "cycloalkylalkyl" as used herein includes groups such as cyclopropylmethyl, cyclobutylmethyl, cyclopentylmethyl and cyclohexylmethyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X preferably represents H, OH or F, more preferably H or F. In one particular embodiment, X is H. In another particular embodiment, X is F. Most preferably, X is H.

In one embodiment, Z represents CH, and thus completes a 1-arylimidazol-4-yl ring. In another embodiment, Z represents N, and thus completes a 1-aryl-1,2,4-triazol-3-yl ring.

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by Ar include pyridyl, pyrazinyl, pyrimidinyl, pyridazinyl and triazinyl, of which pyridyl is a preferred example. Preferably, the phenyl or heteroaryl ring bears 0 to 2 substituents. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a particularly preferred embodiment, Ar represents 4-fluorophenyl.

In a first subset of the compounds of formula I, $R^1$ represents H and the compounds are therefore in accordance with formula IV:

IV

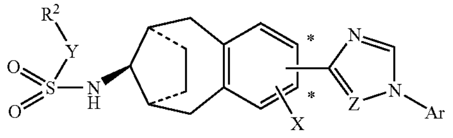

where X, Y, Z, Ar and $R^2$ have the same definitions and preferred identities as indicated above.

Within this subset, hydrocarbon groups represented by $R^2$ include alkyl, cycloalkyl, cycloalkylalkyl, alkenyl, phenyl and benzyl groups optionally bearing up to 3 halogen substituents, the preferred halogen substituent being fluorine or chlorine, especially fluorine. Said alkyl, cycloalkyl, cycloalkylalkyl and alkenyl groups typically comprise up to 6 carbon atoms. Examples of hydrocarbon and fluorinated hydrocarbon groups represented by $R^2$ include 4-fluorophenyl, benzyl, n-propyl, 2,2-dimethylpropyl, n-butyl, isopropyl, t-butyl, 2,2,2-trifluoroethyl, 3,3,3-trifluoropropyl, allyl, cyclobutyl and cyclopropylmethyl.

Heteroaryl groups represented by $R^2$ are either 5-membered or 6-membered and are optionally substituted as defined previously. Preferred 5-membered heteroaryl groups include those containing a sulphur atom, such as thienyl, thiathiazolyl and isothiazolyl. Preferred 6-membered heteroaryl groups include pyridyl, in particular 3-pyridyl. Preferred substituents include halogen (especially chlorine or fluorine), $CF_3$ and alkyl (such as methyl). If two or more substituents are present, preferably not more than one of them is other than halogen or alkyl. Preferred heteroaryl groups are unsubstituted or monosubstituted with halogen.

When $R^2$ represents an optionally substituted phenyl or heteroaryl group, Y is preferably a bond.

When Y represents $NR^3$, $R^2$ may combine with $R^3$ to complete a heterocyclic ring of up to 6 members which is optionally substituted as defined previously. Said ring preferably comprises at most one heteroatom selected from O, N and S in addition to the nitrogen to which $R^2$ and $R^3$ are mutually attached. Suitable rings include azetidinyl, pyrrolidinyl, piperidinyl, piperazinyl, morpholinyl and thiomorpholinyl. Preferred substituents include $CF_3$, halogen (especially chlorine or fluorine) and alkyl such as methyl. If two or more substituents are present, preferably not more than one of them is other than halogen or alkyl.

$R^3$ may alternatively represent H or $C_{1-4}$alkyl, such as methyl. Preferably, $R^3$ represents H or completes a ring with $R^2$.

In one subset of the compounds of formula IV, Y is a bond and $R^2$ is hydrocarbon of up to 6 carbon atoms, optionally bearing up to 3 fluorine or chlorine substituents, or 5- or 6-membered heteroaryl which is optionally substituted as described previously. Within this embodiment, suitable identities for $R^2$ include n-butyl, 4-fluorophenyl, 2-thienyl, 5-chloro-2-thienyl, 5-isothiazolyl and 6-chloro-3-pyridyl.

In a second subset of the compounds of formula IV, Y is O and $R^2$ represents alkyl, alkenyl, cycloalkyl or cycloalkylalkyl of up to 6 carbon atoms which is optionally substituted with up to 3 fluorine atoms.

In a third subset of the compounds of formula IV, Y is NH or NMe and $R^2$ represents alkyl, alkenyl, cycloalkyl or cycloalkylalkyl of up to 6 carbon atoms which is optionally substituted with up to 3 fluorine atoms.

In a fourth subset of the compounds of formula IV, Y represents $NR^3$ and $R^2$ and $R^3$ complete a heterocyclic ring as described previously.

In a second subset of the compounds of formula I Y represents $NR^3$ and $R^1$ and $R^3$ together represent —$CH_2$—, and the compounds are therefore in accordance with formula V:

V

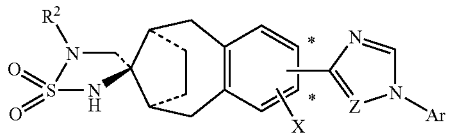

where X, Z, Ar and $R^2$ have the same definitions and preferred identities as indicated previously, with the proviso that when X is H, $R^2$ is not 2,2,2-trifluoroethyl.

Within this subset $R^2$ preferably represents H or a hydrocarbon group of 1-10 carbon atoms which is optionally substituted with up to 3 halogen atoms or with CN or $C_{1-4}$alkoxy, with the proviso that when X is H, $R^2$ does not represent 2,2,2-trifluoroethyl. Suitable hydrocarbon groups represented by $R^2$ include alkyl, cycloalkyl, cycloalkylalkyl, alkenyl, alkynyl and benzyl groups optionally substituted as defined above, the preferred substituents being fluorine or chlorine, especially fluorine, and CN. Said hydrocarbon groups typically comprise up to 6 carbon atoms and are non-aromatic. Examples of groups represented by $R^2$ include H, benzyl, n-propyl, 2,2-dimethylpropyl, n-butyl, isopropyl, t-butyl, 3,3,3-trifluoropropyl, allyl, cyclobutyl, cyclopropylmethyl, 1-methyl-2,2,2-trifluoroethyl, 2-fluoroprop-2-enyl, prop-2-ynyl, 2-methylprop-2-enyl, cyanomethyl and 2-methoxyethyl.

Specific examples of compounds in accordance with the invention include the compounds of formula IIa or formula IIIa in which $R^1$ is H, X is H, Ar is 4-fluorophenyl, and Y, Z, $R^2$ and (where relevant) $R^3$ are as shown in the following table:

| Y | Z | $R^2$ | $R^3$ |
|---|---|---|---|
| bond | CH | n-butyl | — |
| bond | CH | 4-fluorophenyl | — |
| bond | CH | 5-chloro-2-thienyl | — |
| bond | CH | 5-isothiazolyl | — |
| bond | CH | 3,3,3-trifluoropropyl | — |
| $NR^3$ | CH | n-propyl | H |
| $NR^3$ | CH | cyclobutyl | H |
| $NR^3$ | CH | pyrrolidinyl | |
| $NR^3$ | CH | 2,2,2-trifluoroethyl | H |
| $NR^3$ | N | cyclobutyl | H |
| $NR^3$ | N | n-propyl | H |

Further examples of compounds in accordance with the invention include compounds of formula IIa in which Y is $NR^3$, $R^1$ and $R^3$ together represent —$CH_2$—, Ar is 4-fluorophenyl, X is H, and Z and $R^2$ are as indicated in the following table:

| Z | $R^2$ |
|---|---|
| CH | cyclobutyl |
| CH | n-propyl |
| CH | allyl |
| CH | cyclopropyl |
| CH | cyclopropylmethyl |
| CH | 3,3,3-trifluoropropyl |
| CH | isopropyl |
| CH | 2-fluoroprop-2-enyl |
| CH | prop-2-ynyl |
| CH | 2-methylprop-2-enyl |
| CH | H |
| CH | cyanomethyl |
| N | allyl |
| N | cyclopropyl |
| N | cyclobutyl |
| N | n-propyl |
| N | 2-methoxyethyl |
| CH | 1-methyl-2,2,2-trifluoroethyl |

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly (ethylene glycol), poly(vinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The compounds of formula IV may be prepared by reaction of an amine (1) with $R^2$—Y—$SO_2Cl$:

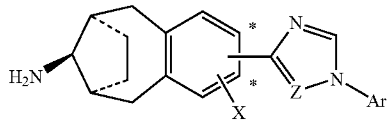

(1)

where X, Y, Z, Ar and $R^2$ have the same meanings as before. The reaction takes place in an aprotic solvent such as dichloromethane in the presence of a base such as triethylamine or pyridine.

The amines (1) may be prepared by treatment of the sulphinamides (2) with acid:

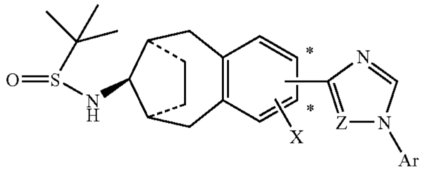

(2)

where X, Ar and Z have the same meanings as before. The reaction may be carried out at 0° C. in methanol solution using anhydrous HCl in dioxan.

The sulphinamides (2) are available from the reduction of imines (3a), which are in turn available from the condensation of ketones (3b) with t-Bu-SO—$NH_2$:

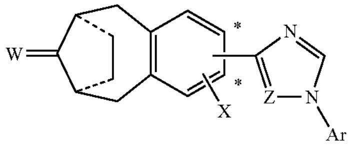

(3)

(a) W = t-Bu—S(O)—N (b) W = O where X, Ar and Z have the same meanings as before. The condensation takes place in refluxing THF in the presence of titanium(IV) ethoxide, while the reduction may be effected using sodium borohydride in methanol at 0° C.

The ketones (3b) may be prepared by coupling of boronates (4) with imidazole or triazole derivatives (5):

(4)

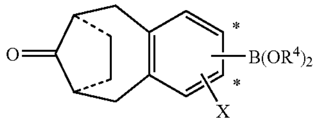

(5)

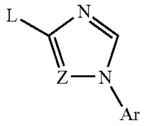

wherein $R^4$ represents H or $C_{1-6}$alkyl, or the two $OR^4$ groups complete a cyclic boronate ester such as the neopentyl glycolate or the pinacolate, L represents a leaving group such as triflate, bromide or iodide, and X, Ar and Z have the same meanings as before. The coupling takes place in the presence of a Pd catalyst such as tetrakis(triphenylphosphine)palladium(0), typically in the presence of an inorganic base such as cesium carbonate, potassium acetate or potassium carbonate in a solvent such as dimethoxyethane or DMF at about 100° C.

Boronates (4) may be prepared by reaction of triflates (6) with a suitable boron reagent, such as bis(pinacolato)diboron or bis(neopentyl glycolato)diboron:

(6)

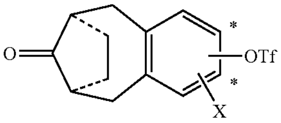

wherein Tf represents trifluoromethanesulphonyl and X has the same meaning as before. The reaction takes place under the same conditions as the coupling of (4) and (5), although the preferred catalyst is [1,1'-bis(diphenylphosphino)ferrocene]dichloropalladium(II).

Triflates (6) are prepared from phenols (7) by reaction with triflic anhydride:

(7)

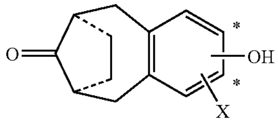

where and X has the same meaning as before. The reaction takes place in dichloromethane solution at 0° C. in the presence of a base such as pyridine.

The phenols (7) in which X is H are known in the literature (J. Org, Chem. 1982, 47, 4329), and the other compounds of formula (7) may be prepared analogously, or by suitable manipulation (e.g. halogenation) of (7) (X=H).

Compounds of formula IV in which Y represents $NR^3$ may also be prepared by condensation of ketones (3b) with $R^2R^3NSO_2NH_2$, followed by reduction of the resulting sulphamoyl imine. The condensation may be carried out by refluxing the reagents in THF in the presence of titanium(IV)

ethoxide for 16 hours, while the reduction may be carried out using sodium borohydride in methanol at 0° C.

A further route to compounds of formula IV in which Y represents O or $NR^3$ comprises reaction of amines (1) with catechol sulphate and treatment of the resulting (2-hydroxyphenyl)sulphamates with $R^2OH$ or $R^2R^3NH$ as appropriate. Alternatively, catechol sulphate may be reacted with $R^2R^3NH$ and the resulting sulphamate reacted with an amine of formula (1).

Compounds of formula V in which $R^2$ is other than H may be prepared by reaction of an aziridine derivative (8a) with $R^{2a}NH_2$:

(8)

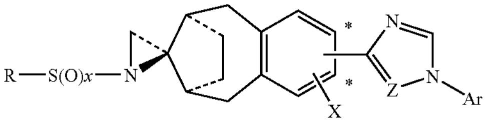

(a) x = 2, R = $NMe_2$
(b) x = 1, R = $^tBu$ wherein Ar, X and Z have the same meanings as before, the imidazole or triazole group is attached at one of the positions indicated by an asterisk and X is attached at a position adjacent thereto, and $R^{2a}$ is $R^2$ that is other than H. The reaction may be carried out by heating the reagents at 100° C. in DMSO in a sealed tube for 16 hours.

Alternatively, the compounds of formula V in which $R^2$ is other than H may be obtained by sequential treatment of an aziridine of formula (8b) with an amine $R^{2a}NH_2$ and then $NH_2SO_2NH_2$. Reaction of (8b) with the amine may be carried out in refluxing 1,2-dichloroethane in the presence of zinc iodide, and reaction of the resulting diamine may with sulfamide may be carried out in refluxing pyridine.

Corresponding compounds wherein $R^2$ is H may be prepared by following one of the procedures described above using p-methoxybenzylamine as the amine $R^{2a}NH_2$, and treating the product with trifluoroacetic acid at ambient temperature to remove the p-methoxybenzyl group.

The aziridines (8a) and (8b) may be prepared by reaction of imines (9a) and (9b) respectively with trimethylsulphoxonium iodide in the presence of sodium hydride:

(9)

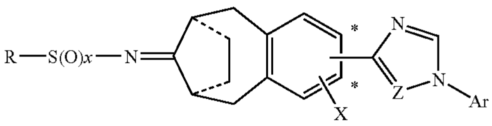

(a) x = 2, R = $NMe_2$
(b) x = 1, R = $^tBu$ where X, Ar and Z have the same meanings as before. The reaction takes place in DMSO at ambient temperature.

The imines (9a) and (9b) may be prepared by condensation of ketones (3b) with, respectively, $Me_2NSO_2NH_2$ or $^tBuSONH_2$. The reaction may be carried out by refluxing the reagents in THF in the presence of titanium (IV) ethoxide for 16 hours.

In an alternative route to the compounds of formula V, imidazole or triazole derivatives (5) are reacted with boronate derivatives (10):

(10)

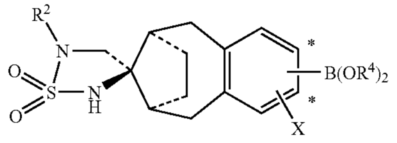

where $R^2$, $R^4$ and X have the same meanings as before. The reaction takes place under the same conditions as the coupling of compounds (4) and (5) described earlier.

The boronates (10) may be prepared from ketones (7) by first converting the ketone group of (7) into a spiro-linked cyclic sulfamide group by the methods described above for the conversion of compounds (3b) into compounds of formula V, and then converting the phenol group into $B(OR^4)_2$ in the manner described above for the conversion of compounds (7) into compounds (4).

The phenol precursors of boronates (10) in which X is H are amenable to chemical manipulation (e.g. fluorination) to provide corresponding compounds in which X is other than H. Alternatively, said phenols may be iodinated to provide the corresponding ortho-iodophenols, which may be transformed into boronates (4) (X═OH) and coupled with imidazoles or triazoles (5) to provide compounds of formula I in which X is OH.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

In a preferred route to enantiomerically pure compounds of formula I, racemic intermediates (7) are subjected to preparative chiral HPLC to provide the corresponding homochiral intermediates, which are then converted to homochiral compounds of formula I by the routes indicated above.

Where they are not commercially available, the starting materials and reagents used in the above-described synthetic schemes may be prepared by conventional means.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

An assay which can be used to determine the level of activity of compounds of the present invention is described in WO01/70677. A preferred assay to determine such activity is described in WO 2004/039800.

Alternative assays are described in *Biochemistry,* 2000, 39(30), 8698-8704.

See also, *J. Neuroscience Methods,* 2000, 102, 61-68.

The compounds of the present invention show unexpectedly high affinities as measured by the above assays. Thus the following Examples all had an $ED_{50}$ of less than 50 nM, typically less than 10 nM, and frequently less than 1 nM in at least one of the above assays. In general, the compounds also exhibit good oral bioavailability and/or brain penetration.

The following examples illustrate the present invention.

EXAMPLE 1

N-{(6S,9R,11R)-2-[1-(4-fluorophenyl)-1H-imidazol-4-yl]-5,6,7,8,9,10-hexahydro-6,9-methanobenzo[α][8]annulen-11-yl}-N'-(2,2,2-trifluoroethyl)sulfamide

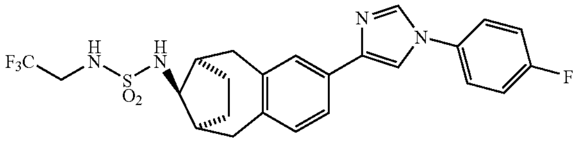

Step 1

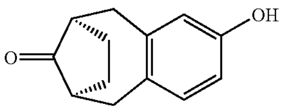

2-Hydroxy-5,6,7,8,9,10-hexahydro-6,9-methanobenzo[α][8]annulen-11-one (J. Org. Chem 1982, 47, 4329) was resolved using a Berger SFC semi-preparative instrument (chiralpak AS (25×2 cm, 20 um); 15% MeOH/$CO_2$ @50 mL/min; 35□C; 100 bar; second eluted enantiomer).

Step 2

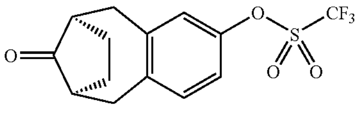

To a stirred solution of the product from Step 1 (6.83 g, 34 mmol) in dry DCM (40 mL) at 0° C. under nitrogen was added pyridine (3.8 mL, 47 mmol) followed by triflic anhydride (8.0 mL, 47 mmol). The reaction was stirred at 0° C. for 2 hours. Water (40 mL) was added and the layers were separated. The aqueous layer was extracted with DCM (×2). The combined extracts were washed with brine (×1), then dried ($MgSO_4$), filtered and evaporated. The residue was purified by chromatography on silica, eluting with 10-15% EtOAc/hexane, to give the triflate (9.64 g, 85%). (400 MHz $^1H$, δ-$CDCl_3$) 1.28 (2H, m), 1.92 (2H, m), 2.64 (2H, m), 2.85-3.05 (4H, m), 7.13 (2H, m), 7.29 (1H, m).

Step 3

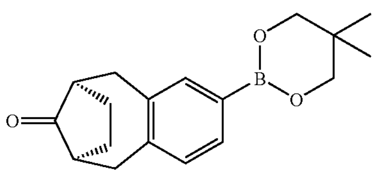

A solution of the triflate from Step 2 (2.546 g, 7.6 mmol), bis(neopentyl glycolato)diboron (2.064 g, 9.1 mmol) and KOAc (1.495 g, 15.2 mmol) in dioxane (27 mL) and DMSO (3 mL) was deoxygenated by bubbling nitrogen through the solution for 20 minutes. [1,1'-Bis(diphenylphosphino)ferrocene] palladium (II) chloride (0.622 g, 0.76 mmol) was added and deoxygenation was continued for a further 10 minutes. The reaction was heated at 90° C. for 16 hours, then allowed to cool and diluted with water (40 mL). The reaction was extracted with EtOAc (×3). The combined extracts were washed with water then brine, dried ($MgSO_4$), filtered and evaporated. The residue was purified by chromatography on silica, eluting with 20% EtOAc/hexane to give the product (1.881 g, 83%). (360 MHz $^1H$, δ-$CDCl_3$) 1.04 (6H, s), 1.30 (2H, m), 1.83 (2H, m), 2.59 (2H, m), 2.85-3.00 (4H, m), 3.78 (4H, s), 7.19 (1H, m), 7.62 (2H, m).

Step 4

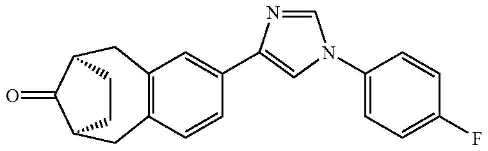

A solution of the boronate from Step 3 (1.787 g, 6.0 mmol), 4-bromo-1-(4-fluorophenyl)-1H-imidazole (1.589 g, 6.6 mmol), and cesium carbonate (4.296 g, 13.2 mmol) in DME (20 mL) and water (10 mL) was deoxygenated by bubbling nitrogen through the solution for 30 minutes. Tetrakis(triphenylphosphine)palladium (0) (0.693 g, 0.6 mmol) was added and deoxygenation was continued for a further 10 minutes. The reaction was heated at 90° C. for 16 hours then allowed to cool and diluted with water (40 mL). The catalyst was removed by filtration through Hyflo□ and the filtrate was extracted with EtOAc (×3). The combined extracts were washed with water then brine, dried ($MgSO_4$), filtered and evaporated. The residue was purified by chromatography on silica, eluting with 40% EtOAc/hexane. The resulting solid was washed with ether to give the product (1.818 g, 88%). (360MHz $^1H$, δ-$CDCl_3$) 1.36 (2H, m), 1.87 (2H, m), 2.61 (2H, m), 2.89-3.09 (4H, m), 7.23 (3H, m), 7.42 (2H, m), 7.51 (1H, s), 7.62 (1H, m), 7.73 (1H, s), 7.83 (1H, s).

Step 5

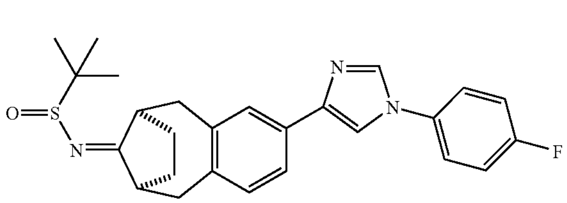

1,1-Dimethylethylsulfinamide (814 mg, 6.4 mmol) followed by titanium tetraethoxide (tech., 1.2 ml, 5.8 mmol) were added to a solution of the ketone from Step 4 (1.0 g, 2.8 mmol) in THF (20 ml), under a nitrogen atmosphere, and the mixture was heated at reflux for 20 hours. The mixture was cooled to room temperature and poured onto rapidly stirring brine. After 30 minutes ethyl acetate (100 ml) was added and the mixture was filtered through Hyflo®, the phases were separated and the aqueous layer extracted with ethyl acetate (100 ml). The organics were washed with brine, dried ($MgSO_4$) and evaporated in vacuo to give the desired imine as a yellowish foam (1.3 g, 99%) M/Z ES+ (450) $(MH)^+$.

Step 6

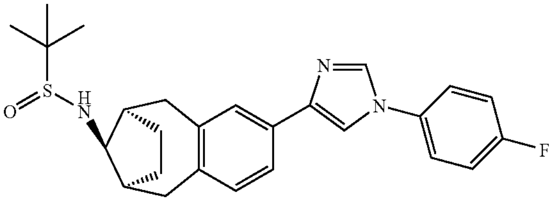

A solution of the imine from Step 5 (1.3 g, 2.8 mmol) in methanol (40 ml) at 0° C., under a nitrogen atmosphere, was treated with sodium borohydride (220 mg, 5.8 mmol) and the mixture was stirred at 0° C. for two hours. The reaction was concentrated in vacuo, the residue was diluted with water (40 ml) and extracted with ethyl acetate (2×40 ml). The organics were washed with brine, dried ($MgSO_4$) and evaporated in vacuo to give the desired sulfinamide as a brown foam (1.4 g, 99%) M/Z ES+ (452) $(MH)^+$.

Step 7

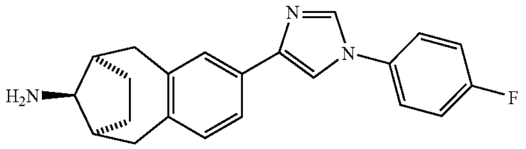

A solution of the sulfinamide from Step 6 (1.4 g, 2.9 mmol) in anhydrous methanol (20 ml) at 0° C. was treated with hydrogen chloride (4N in dioxane, 8 ml, 32 mmol) and the reaction was stirred at 0° C. for two hours. After evaporation in vacuo, the residue was diluted with sodium bicarbonate (sat, 40 ml) and extracted with ethyl acetate (2×40 ml). The organics were washed with brine, dried ($MgSO_4$) and evaporated in vacuo to a brown gum which was purified by ion exchange chromatography (SCX, washing with methanol and eluting with ammonia in methanol (2M)) to give the desired amine as a colourless foam (925 mg, 93%). M/Z ES+ (348) $(MH)^+$.

Step 8

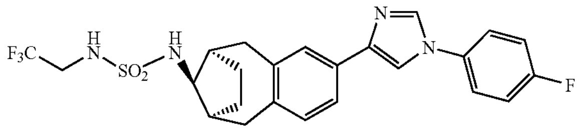

A solution of the amine from Step 7 (50 mg, 0.14 mmol) in dichloromethane (1 ml) was added to 2,2,2-trifluoroethylsulfamoyl chloride (138 mg, 0.7 mmol), then triethylamine (195

μl, 1.4 mmol) was added and the mixture was stirred at room temperature for 16 hours. The reaction was quenched by the addition of $NaHCO_3$ (sat, 1.5 ml) and the phases were separated via Bond Elute™ phase separation cartridge. The aqueous phase was extracted with dichloromethane (3×1 ml) and the combined organics were evaporated in vacuo and purified by chromatography on silica [ethylacetate:isohexane 1:2] to give the desired sulfamide as a colourless foam (41 mg, 58%). NMR ($CDCl_3$) δ 1.21-1.32 (2H, m), 1.70-1.74 (2H, m), 2.50-2.59 (2H, m), 2.65-2.77 (2H, m), 3.08 (2H, dd, J=16.1 & 5.6 Hz), 3.71-3.84 (3H, m), 4.76 (1H, t, J=7.0 Hz, NH), 4.82 (1H, d, J=7.9 Hz, NH), 7.12 (1H, d, J=7.8 Hz), 7.17-7.23 (2H, m), 7.39-7.44 (2H, m), 7.48 (1h, d, J=1.4 Hz), 7.52 (1H, dd, J=7.7 & 1.4 Hz), 7.61 (1H, s) and 7.83 (1H, d, J=1.2 Hz). M/Z ES+ (509) $(MH)^+$.

EXAMPLES 2-9

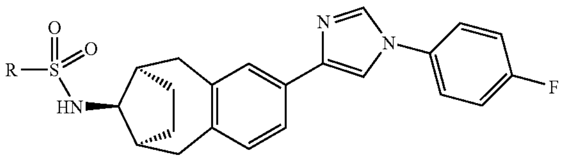

The following examples were prepared by the method described in Example 1, using the appropriate sulfamoyl* or sulfonyl chloride in the final step:

| Example | R | m/z $(MH)^+$ |
|---|---|---|
| 2 | 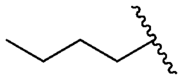 | 468 |
| 3 | 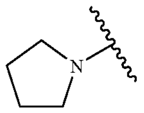 | 481 |
| 4 | 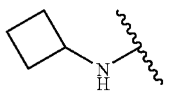 | 481 |
| 5 | 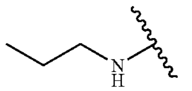 | 469 |
| 6 | 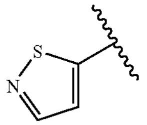 | 495 |
| 7 | 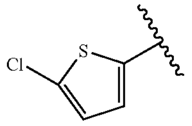 | 529 |

-continued

| Example | R | m/z $(MH)^+$ |
|---|---|---|
| 8 | 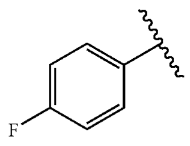 | 506 |
| 9 | 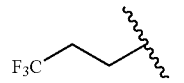 | 508 |

*Where the sulfamoyl chlorides were not commercially available, a typical preparation was as follows: A solution of pyrrolidine (13.4 ml, 160 mmol) in dry toluene (40 ml) was added dropwise to a cold (−10° C.) solution of sulfuryl chloride in toluene (30 ml) at such a rate that the internal temperature did not exceed −5° C. Once the addition was complete the mixture was stirred at −5° C. for thirty minutes before water (50 ml) was added. The layers were separated and the organic layer was washed with HCl (2N, 50 ml), dried ($MgSO_4$) and evaporated in vacuo to a clear oil (9.6 g). The oil was a 2:1 mixture of the desired sulfamoyl chloride and bis-pyrrolidine sulfamide. NMR ($CDCl_3$) δ 1.89-1.93 (4H, m, sulfamide), 1.99-2.05 (4H, m, sulfamoyl chloride), 3.29-3.33 (4H, m, sulfamide) and 3.48-3.52 (4H, m, sulfamoyl chloride).

EXAMPLE 10

N-cyclobutyl-N'-{(6S,9R,11R)-2-[1-(4-fluorophenyl)-1H-1,2,4-triazol-3-yl]-5,6,7,8,9,10-hexahydro-6,9-methanobenzo[8]annulen-11-yl}sulfamide

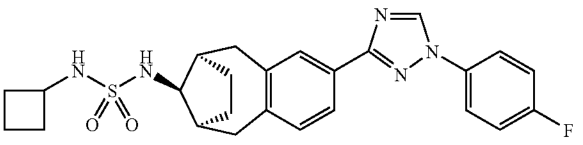

Step 1

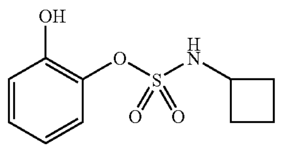

Catechol sulfate (25 g, 144 mmol) was added to stirred solution of cyclobutylamine (8.6 g, 120 mmol) in dry THF (60 ml) at room temperature under nitrogen (mild exotherm—cooled with water bath). After 16 hours the reaction was diluted with saturated aqueous $NH_4Cl$ (300 ml) and then extracted with ethyl acetate (2×200 ml). The combined extracts were washed with brine, dried ($MgSO_4$), filtered and evaporated. The residue was purified by chromatography on silica, eluting with 5% EtOAc/DCM to give the sulfamate as an off-white solid (17 g, 58%). (400 MHz $^1H$, δ-$CDCl_3$) 1.65-1.78 (2H, m), 1.94-2.04 (2H, m), 2.32-2.40 (1H, m), 4.90 (1H, br, d, J=8.1), 6.16 (1H, s), 6.89-6.94 (1H, m), 7.04-7.07 (1H, m), 7.16-7.21 (2H, m).

Step 2

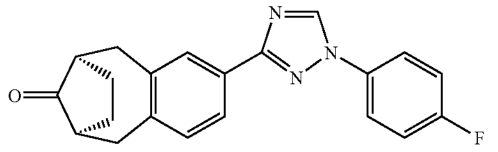

A solution of the boronate from Example 1, Step 3 (3.904 g, 13 mmol), 3-bromo-1-(4-fluorophenyl)-1H-1,2,4-triazole (2.881 g, 12 mmol), and cesium carbonate (7.756 g, 24 mmol) in DME (40 mL) and water (20 mL) was deoxygenated by bubbling nitrogen through the solution for 10 minutes. Tetrakis(triphenylphosphine)palladium(0) (1.375 g, 1.2 mmol) was added and deoxygenation was continued for a further 10 minutes. The reaction was heated at 90° C. for 16 hours then allowed to cool and diluted with water (40 mL). The catalyst was removed by filtration through Hyflo□ and the filtrate was extracted with EtOAc (×3). The combined extracts were washed with water then brine, dried ($MgSO_4$), filtered and evaporated. The residue was purified by chromatography on silica, eluting with 20-50% EtOAc/hexane, to give the product (2.906 g, 70%). (360MHz $^1H$, δ-$CDCl_3$) 1.36 (2H, m), 1.88 (2H, m), 2.63 (2H, m), 2.93-3.10 (4H, m), 7.22 (2H, m), 7.31 (1H, m), 7.73 (2H, m), 8.01 (1H, m), 8.05 (1H, s), 8.52 (1H, s). MS (ES+) 348, $MH^+$.

Step 3

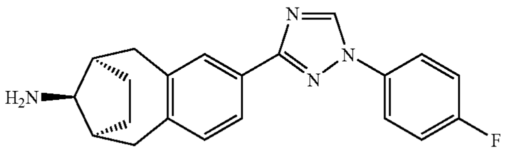

The amine was made from the ketone of Step 2 by the method of Example 1 Steps 5 to 7. MS (ES+) 349, $MH^+$.

Step 4

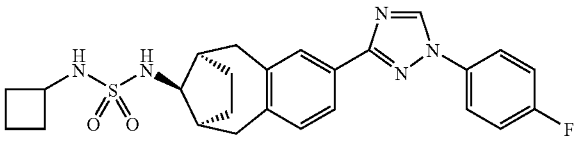

A solution of the amine from Step 3 (86 mg, 0.25 mmol), triethylamine (37 mg, 0.37 mmol) and the sulfamate from Step 1 (90 mg, 0.37 mmol) in dioxane (2 mL) was heated at 80° C. for 16 hours. The reaction was allowed to cool to room temperature and concentrated in vacuo. The residue was taken up into EtOAc (20 mL) and washed with 2N NaOH (10 mL) then brine (10 mL), dried ($MgSO_4$), filtered and evaporated. The residue was purified by chromatography on silica, eluting with 15% EtOAc/hexane, to give the title compound (113 mg, 95%). (360 MHz $^1H$, δ-$CDCl_3$) 1.23 (2H, m), 1.72 (3H, m), 1.97 (3H, m), 2.39 (2H, m), 2.51 (2H, m), 2.66-2.81 (2H, m), 3.14 (2H, m), 3.76 (1H, m), 3.90 (1H, m), 4.45 (1H, m), 4.67 (1H, m), 7.23 (3H, m), 7.73 (2H, m), 7.90 (2H, m), 8.57 (1H, s). MS (ES+) 482, $MH^+$.

EXAMPLE 11

N-{(6S,9R,11R)-2-[1-(4-fluorophenyl)-1H-1,2,4-triazol-3-yl]-5,6,7,8,9,10-hexahydro-6,9-methanobenzo[8]annulen-11-yl}-N'-propylsulfamide

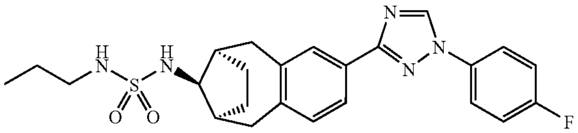

The title compound was made by the method of Example 10, using n-propylamine instead of cyclobutylamine in Step 1. MS (ES+) 470, $MH^+$.

EXAMPLE 12

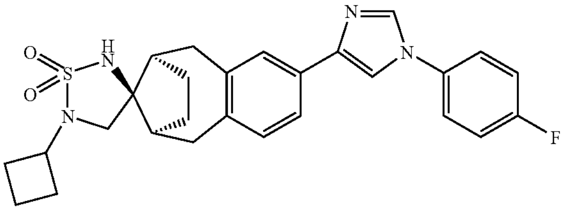

Step 1

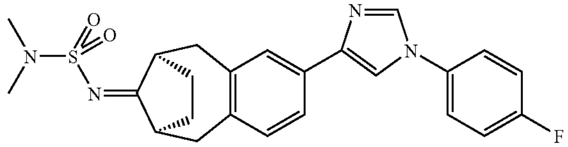

A solution of the ketone from Example 1 Step 4 (0.936 g, 2.7 mmol), N,N-dimethylsulfamide (1.677 g, 13.5 mmol) and titanium (IV) ethoxide (tech., 1.7 mL, 8.1 mmol) in dry THF (15 mL) was stirred and heated at reflux under nitrogen for 16 hours. The reaction was allowed to cool to room temperature and poured into rapidly stirred brine (50 mL). The mixture was stirred for 30 minutes, then filtered through Hyflo®, washing with DCM. The filtrate was transferred to a separating funnel. The layers were separated, and the aqueous layer was extracted with DCM. The combined organic extracts were washed with 2N NaOH then brine, dried ($MgSO_4$), filtered and evaporated. The residue was purified by chromatography on silica, eluting with 10-20% EtOAc/DCM, to give the imine (0.960 g, 78%). (360 MHz $^1H$, 6-$CDCl_3$) 1.26-1.50 (2H, m), 1.75-1.85 (2H, m), 2.90 (6H, s), 2.94 (2H, m), 3.09 (3H, m), 3.89 (1H, m), 7.22 (3H, m), 7.42 (2H, m), 7.51 (1H, s), 7.65 (1H, m), 7.73 (1H, s), 7.83 (1H, m).

Step 2

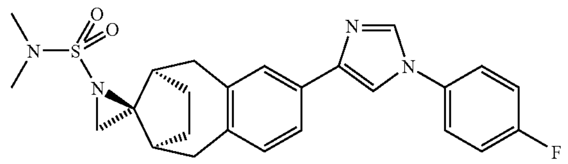

Sodium hydride (60% dispersion in oil, 0.127 g, 3.2 mmol) was added portionwise to a stirred suspension of trimethyl sulfoxonium iodide (0.700 g, 3.2 mmol) in dry DMSO (5 mL)

at room temperature under nitrogen. After 1 hour at room temperature, a solution of the imine from Step 1 (0.960 g, 2.1 mmol) in dry DMSO (10 mL) was added. The mixture was stirred at room temperature for 2 hours, then quenched with water (20 mL). The reaction was extracted with EtOAc. The combined organic extracts were washed with water then brine, dried ($MgSO_4$), filtered and evaporated. The residue was purified by chromatography on silica, eluting with 50-60% EtOAc/hexane, to give the aziridine (0.847 g, 86%). (360MHz $^1H$, δ-$CDCl_3$) 1.31 (2H, m), 1.74 (2H, m), 2.24 (2H, m), 2.45 (2H, m), 2.73-2.86 (2H, m), 2.97 (6H, s), 3.59 (2H, m), 7.13 (1H, m), 7.20 (2H, m), 7.42 (2H, m), 7.48 (1H, s), 7.54 (1H, m), 7.60 (1H, s), 7.83 (1H, s).

Step 3

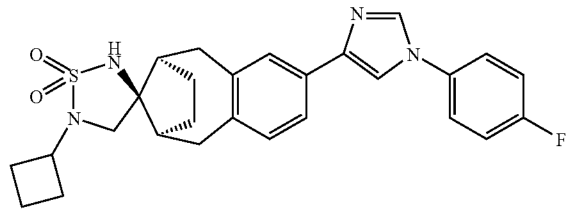

A solution of the aziridine from Step 2 (60 mg, 0.13 mmol) and cyclobutylamine (46 mg, 0.65 mmol) in DMSO (2 mL) was stirred and heated at 100° C. in a sealed tube for 16 hours. The reaction was allowed to cool to room temperature then diluted with EtOAc (20 mL) and washed with water (2×10 mL) then brine (10 mL), dried ($MgSO_4$), filtered and evaporated. The residue was purified by chromatography on silica, eluting with 60% EtOAc/hexane, to give the title compound (52 mg, 82%). (360 MHz $^1H$, δ-$CDCl_3$) 1.34 (2H, m), 1.70 (2H, m), 1.83 (2H, m), 2.23 (4H, m), 2.44 (2H, m), 2.67-2.80 (2H, m), 3.19 (4H, m), 3.81 (1H, quintet, J=8.0), 4.68 (1H, s), 7.12 (1H, m), 7.20 (2H, m), 7.41 (2H, m), 7.48 (1H, s), 7.53 (1H, m), 7.61 (1H, s), 7.82 (1H, s). MS (ES+) 493, $MH^+$.

The compounds in table 1 were prepared by the same method as Example 12, using the appropriate amine instead of cyclobutylamine in Step 3.

TABLE 1

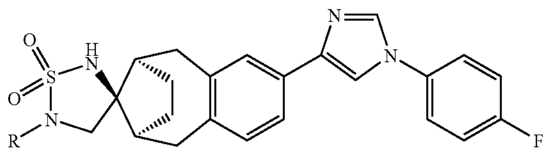

| Example | R | m/z $(M + H)^+$ |
|---|---|---|
| 13 | nPr | 481 |
| 14 | 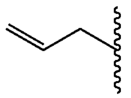 | 479 |
| 15 | 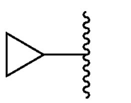 | 479 |
| 16 | 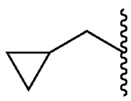 | 493 |

TABLE 1-continued

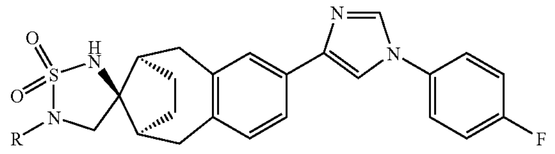

| Example | R | m/z $(M + H)^+$ |
|---|---|---|
| 17 | 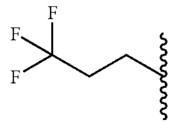 | 535 |
| 18 | 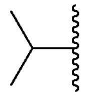 | 481 |
| 19 | 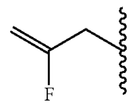 | 497 |
| 20 | 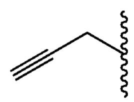 | 477 |
| 21 | 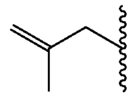 | 493 |

EXAMPLE 22

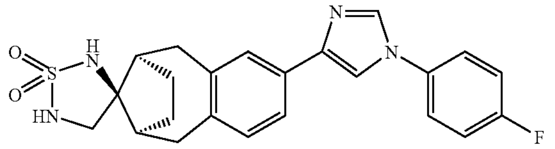

A solution of the aziridine from Example 12, Step 2 (120 mg, 0.26 mmol) and 4-methoxybenzylamine (176 mg, 1.28 mmol) in DMSO (4 mL) was stirred and heated at 100° C. in a sealed tube for 16 hours. The reaction was allowed to cool to room temperature then diluted with EtOAc (40 mL) and washed with water (2×20 mL) then brine (20 mL), dried ($MgSO_4$), filtered and evaporated. The residue was purified by chromatography on silica, eluting with 50% EtOAc/hexane to give the sulfamide (134 mg). A solution of the sulfamide and TFA (5 mL) in DCM (5 mL) was stirred at room temperature for 6 hours. The reaction was concentrated in vacuo and saturated sodium bicarbonate solution (10 mL) was added. The reaction was extracted with DCM, the combined organic extracts were washed with brine, dried ($MgSO_4$), filtered and evaporated. The residue was purified by chromatography on silica, eluting with 50-70% EtOAc/hexane, to give the title compound (86 mg, 76%). (360 MHz $^1H$, δ-$CDCl_3$) 1.35 (2H, m), 1.69 (2H, m), 2.41 (2H, m), 2.70-2.83 (2H, m), 3.24 (2H, m), 3.37 (2H, d, J=7.4), 4.62

(1H, t, J=7.3), 4.79 (1H, s), 7.12 (1H, m), 7.20 (2H, m), 7.41 (2H, m), 7.48 (1H, s), 7.53 (1H, m), 7.60 (1H, s), 7.82 (1H, s). MS (ES+) 439, $MH^+$.

EXAMPLE 23

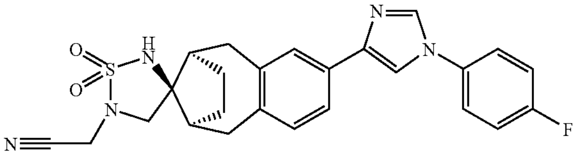

The procedure of Example 12 was repeated, substituting glycinamide for cyclobutylamine in the final step.

A solution of the resulting sulfamide (50 mg, 0.1 mmol) in phosphorous oxychloride (3 mL) was stirred and heated under reflux for 2 hours. The reaction was allowed to cool to room temperature and concentrated in vacuo. Saturated sodium bicarbonate solution (20 mL) was added. The reaction was extracted with DCM, the combined organic extracts were washed with brine, dried ($MgSO_4$), filtered and evaporated. The residue was purified by chromatography on silica, eluting with EtOAc, to give the title compound (46 mg, 96%). (360 MHz $^1H$, δ-$CDCl_3$) 1.40 (2H, m), 1.74 (2H, m), 2.50 (2H, m), 2.69-2.83 (2H, m), 3.20 (2H, m), 3.42 (2H, s), 4.04 (2H, s), 4.90 (1H, s), 7.12 (1H, m), 7.21 (2H, m), 7.42 (2H, m), 7.48 (1H, m), 7.54 (1H, m), 7.61 (1H, s), 7.83 (1H, s). MS (ES+) 478, $MH^+$.

EXAMPLES 24-28

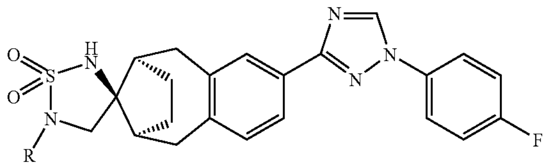

Step 1

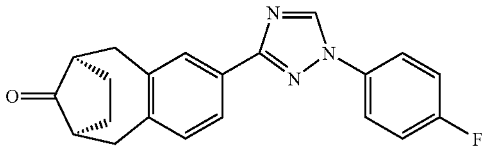

A solution of the boronate from Example 1, Step 3 (3.904 g, 13 mmol), 3-bromo-1-(4-fluorophenyl)-1H-1,2,4-triazole (2.881 g, 12 mmol), and cesium carbonate (7.756 g, 24 mmol) in DME (40 mL) and water (20 mL) was deoxygenated by bubbling nitrogen through the solution for 10 minutes. Tetrakis(triphenylphosphine)palladium (0) (1.375 g, 1.2 mmol) was added and deoxygenation was continued for a further 10 minutes. The reaction was heated at 90° C. for 16 hours then allowed to cool and diluted with water (40 mL). The catalyst was removed by filtration through Hyflo® and the filtrate was extracted with EtOAc (×3). The combined extracts were washed with water then brine, dried ($MgSO_4$), filtered and evaporated. The residue was purified by chromatography on silica, eluting with 20-50% EtOAc/hexane, to give the product (2.906 g, 70%). (360 MHz $^1H$, δ-$CDCl_3$) 1.36 (2H, m), 1.88 (2H, m), 2.63 (2H, m), 2.93-3.10 (4H, m), 7.22 (2H, m), 7.31 (1H, m), 7.73 (2H, m), 8.01 (1H, m), 8.05 (1H, s), 8.52 (1H, s). MS (ES+) 348, $MH^+$.

Step 2

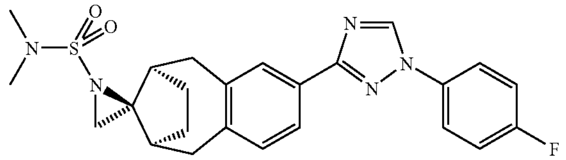

A solution of the ketone from Step 1 (2.000 g, 5.8 mmol), N,N-dimethylsulfamide (2.859 g, 23 mmol) and titanium (TV) ethoxide (tech., 2.4 mL, 11 mmol) in dry THF (20 mL) was stirred and heated at reflux under nitrogen for 16 hours. The reaction was allowed to cool to room temperature and poured into rapidly stirred brine (50 mL). The mixture was stirred for 10 minutes, then filtered through Hyflo®, washing with EtOAc. The filtrate was transferred to a separating funnel. The layers were separated, and the aqueous layer was extracted with EtOAc. The combined organic extracts were washed with brine, dried ($MgSO_4$), filtered and evaporated. The residue was purified by chromatography on silica, eluting with 10% EtOAc/DCM, to give the imine (3.571 g, contains N,N-dimethylsulfamide).

Sodium hydride (60% dispersion in oil, 0.345 g, 8.6 mmol) was added portionwise to a stirred suspension of trimethyl sulfoxonium iodide (1.900 g, 8.6 mmol) in dry DMSO (20 mL) at room temperature under nitrogen. After 1 hour at room temperature, a solution of the imine (3.571 g) in dry DMSO (30 mL) was added. The mixture was stirred at room temperature for 2 hours, then quenched with water (60 mL). The reaction was extracted with EtOAc. The combined organic extracts were washed with water then brine, dried ($MgSO_4$), filtered and evaporated. The residue was purified by chromatography on silica, eluting with 50% EtOAc/hexane, to give the aziridine (2.424 g, 90%). (360 MHz $^1H$, δ-$CDCl_3$) 1.27 (2H, m), 1.74 (2H, m), 2.24 (2H, m), 2.45 (2H, m), 2.85 (2H, m), 2.97 (6H, s), 3.62 (2H, m), 7.22 (3H, m), 7.72 (2H, m), 7.91 (2H, m), 8.50 (1H, s).

The compounds in Table 2 were prepared from the aziridine in Step 2 by the same method as for Example 12, Step 3 using the appropriate amine.

TABLE 2

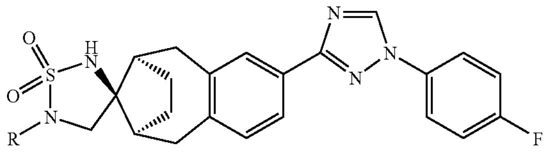

| Example | R | m/z $(M + H)^+$ |
|---|---|---|
| 24 | 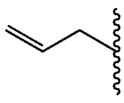 | 480 |
| 25 | 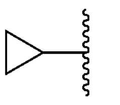 | 480 |

TABLE 2-continued

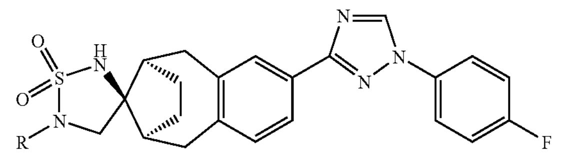

| Example | R | m/z (M + H)+ |
|---|---|---|
| 26 | 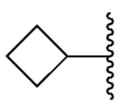 | 494 |
| 27 | nPr | 482 |
| 28 | 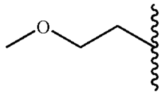 | 498 |

EXAMPLE 29

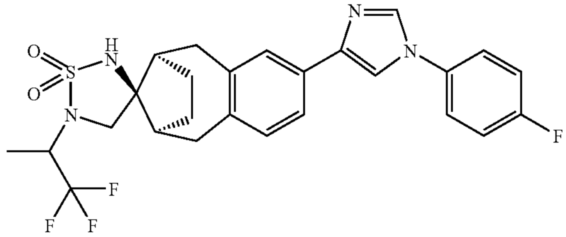

Step 1

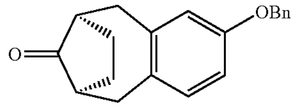

A mixture of homochiral 2-hydroxy-5,6,7,8,9,10-hexahydro-6,9-methanobenzo[a][8]annulen-11-one (15 g; Example 1 Step 1), $K_2CO_3$ (20.5 g) and benzyl bromide (10.6 ml) in DMF (100 ml) was stirred for 48 hrs at room temperature. The reaction was diluted with water (500 ml) and extracted with EtOAc (3×150 ml). The combined organic phases were washed with water (2×300 ml), brine (150 ml), dried and concentrated to give a gummy oil which crystallized on standing and after trituration with ether gave the title benzyl ether (19.5 g, 90%) as a white solid.

Step 2

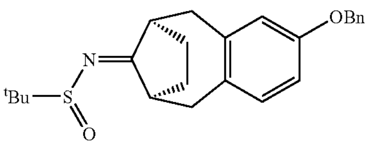

A solution of the product from Step 1 (20 g, 68 mmol), (+/−)tert-butyl sulfinamide (9.2 g, 76 mmol) and titanium (IV) ethoxide (tech., 29.2 mL, 140 mmol) in dry THF (140 mL) was stirred and heated at reflux under nitrogen for 4 hours. The reaction was allowed to cool to room temperature and poured into rapidly stirred brine (160 mL). The mixture was stirred for 20 minutes, then filtered through Hyflo□, washing with ethyl acetate. The filtrate was transferred to a separating funnel. The layers were separated, and the aqueous layer was extracted with ethyl acetate (×1). The combined organic extracts were washed with brine, then dried ($Na_2SO_4$), filtered and evaporated. The residue was purified by chromatography on silica, eluting with 20→30% ethyl acetate/hexanes, to give the imine (24.9 g, 93%) as a colourless solid. MS (ES+) 396 ($[MH]^+$).

Step 3

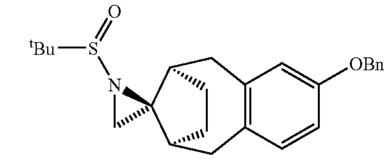

Sodium hydride (60% dispersion in oil, 3.8 g, 95 mmol) was added portionwise to a stirred suspension of trimethyl sulfoxonium iodide (21 g, 95 mmol) in dry DMSO (150 mL) at room temperature under nitrogen. After 90 minutes at room temperature, a solution of the product from Step 2 (24.9 g, 95 mmol) in dry DMSO (250 mL) was added such that the internal temperature remained below 30° C. The mixture was stirred at room temperature for 4 hours, then quenched with water (1 L). The precipitate was collected by filtration. The solid was taken up in dichloromethane and washed with brine. The organic layer was dried ($Na_2SO_4$), filtered and evaporated. The residue was purified by chromatography on silica, eluting with 5→10% ethyl acetate/dichloromethane, to give the aziridine (23.2 g, 90%) as a colourless solid. MS (ES+) 410 ($[MH]^+$).

Step 4

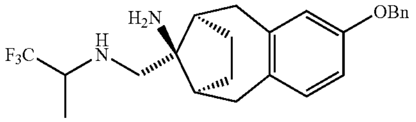

1-(Trifluoromethyl)ethyl amine (2 mL) was added to a stirred suspension of the aziridine (1.000 g, 2.4 mmol) and anhydrous zinc iodide (0.779 g, 2.4 mmol) in dry 1,2-dichloroethane (5 mL) at room temperature under nitrogen. The resulting solution was heated at 80° C., protected from light for 24 hours. Saturated sodium bicarbonate solution (10 mL) was added. The reaction was extracted with DCM, the combined organic extracts were washed with brine, dried ($MgSO_4$), filtered and evaporated. The residue was purified by chromatography on silica, eluting with 5% methanol/DCM, to give the diamine (0.707 g, 69%). MS(ES+) 419, $MH^+$.

Step 5

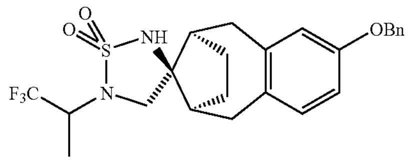

A solution of the product from Step 4 (0.701 g, 1.68 mmol) and sulfamide (0.209 g, 2.17 mmol) in dry pyridine (20 mL)

was stirred and heated at reflux for 16 hours. The reaction was allowed to cool, then the pyridine was removed in vacuo. 2N HCl was added and the reaction was extracted with EtOAc. The combined organic extracts were washed with brine, dried ($MgSO_4$), filtered and evaporated. The residue was purified by chromatography on silica, eluting with 20% EtOAc/hexane, to give the cyclic sulfamide (0.674 g, 84%). $^1H$ NMR (360 MHz, $CDCl_3$) $\delta_H$ 1.34 (2H, d, J=9.3), 1.45 (3H, d, 7.0), 1.69 (2H, m), 2.45 (2H, m), 2.62 (2H, m), 3.04-3.34 (2H, m), 3.34 (2H, s), 4.18 (1H, m), 4.62 (1H, m), 5.03 (2H, s), 6.73 (2H, m), 6.99 (1H, m), 7.35 (5H, m).

Step 6

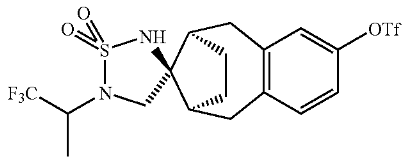

A solution of the product from Step 5 (0.652 g, 1.4 mmol) in EtOAc (40 mL) was hydrogenated at 50 psi over 10% palladium on carbon (65 mg) for 16 hours at room temperature. The catalyst was removed by filtration through Hyflo®. The filtrate was evaporated to give the phenol (0.521 g, 98%). Trifluoromethanesulfonic anhydride (0.3 ml, 1.78 mmol) was added dropwise to a solution of the phenol (0.521 g, 1.33 mmol) and pyridine (0.22 mL, 2.72 mmol) in DCM (15 ml) at 0° C. The mixture was stirred at room temperature for four hours. The reaction was diluted with water (20 ml) and extracted with DCM. The combined organic extracts were washed with brine, dried ($MgSO_4$), filtered and evaporated. The residue was purified by chromatography on silica, eluting with 10-20% EtOAc/hexane, to give the two diastereoisomers of the triflate in a 1:1 ratio (0.621 g, 89%).

Diastereoisomer 1, $^1H$ NMR (360 MHz, $CDCl_3$) $\delta_H$ 1.29 (2H, m), 1.45 (3H, d, J=7.0) 1.75 (2H, m), 2.48 (2H, m), 2.71 (2H, m), 3.17 (1H, d, J=15.9), 3.32 (1H, m), 3.35 (2H, s), 4.20 (1H, m), 4.74 (1H, s), 7.03 (2H, m), 7.17 (1H, m).

Diastereoisomer 2, $^1H$ NMR (360 MHz, $CDCl_3$) $\delta_H$ 1.27 (2H, m), 1.46 (3H, d, J=7.0), 1.76 (2H, m), 2.46 (2H, m), 2.72 (2H, m), 3.21 (1H, d, J=15.8), 3.30 (1H, d, J=15.8), 3.35 (2H, s), 4.20 (1H, m), 4.62 (1H, s), 7.04 (2H, m), 7.17 (1H, m).

Step 7

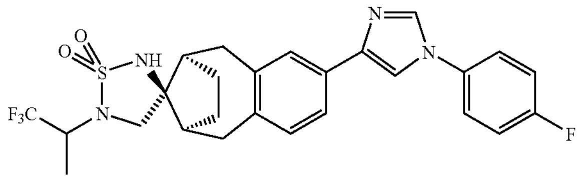

Diastereoisomer 1 from Step 6 was taken through Steps 3 and 4 in Example 1 to give the title compound (63 mg). (500 MHz $^1H$, $\delta$-$CDCl_3$) 1.38 (2H, m), 1.46 (3H, d, J=7.0), 1.70 (2H, m), 2.46 (2H, m), 2.73 (2H, m), 3.17 (1H, d, J=16.0), 3.31 (1H, d, J=15.9), 3.36 (2H, s), 4.20 (1H, m), 4.77 (1H, s), 7.12 (1H, m), 7.21 (2H, m), 7.43 (2H, m), 7.49 (1H, s), 7.54 (1H, m), 7.63 (1H, s), 7.89 (1H, s). MS (ES+) 535, $MH^+$.

Diastereoisomer 2 from Step 6 was taken through Steps 3 and 4 in Example 1 to give the title compound (69 mg). MS (ES+) 535, $MH^+$.

The invention claimed is:

1. A compound of formula I:

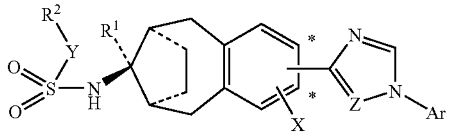

I wherein Z represents CH or N and the resulting imidazole or triazole group is attached at one of the positions indicated by an asterisk and X is attached at a position adjacent thereto;

X represents H, OH, $C_{1-4}$alkoxy, Cl or F;

Y represents a bond, O or $NR^3$;

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

$R^1$ represents H; or when Y represents $NR^3$, $R^1$ and $R^3$ may together represent —$CH_2$—;

$R^2$ represents H or a hydrocarbon group of 1-10 carbon atoms which is optionally substituted with CN, $C_{1-4}$alkoxy or up to 3 halogen atoms; or $R^2$ represents heteroaryl of 5 or 6 ring atoms optionally bearing up to 3 substituents independently selected from halogen, $CF_3$, $CHF_2$, $CH_2F$, $NO_2$, CN, $OCF_3$, $C_{1-6}$alkyl and $C_{1-6}$alkoxy; or when Y represents $NR^3$, $R^2$ and $R^3$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy; and $R^3$ represents H or $C_{1-4}$alkyl, or together with $R^2$ completes a heterocyclic ring as defined above;

or together with $R^1$ represents —$CH_2$—;

provided that when X is H, and Y represents $NR^3$ and $R^1$ and $R^3$ together represent —$CH_2$—, $R^2$ does not represent 2,2,2-trifluoroethyl; and provided that $R^1$ and $R^2$ are not both H;

or a pharmaceutically acceptable salt thereof.

2. A compound according to claim 1 according to formula IV:

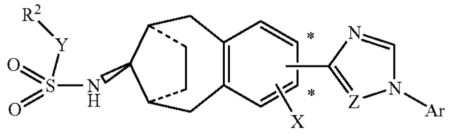

IV or a pharmaceutically acceptable salt thereof, where X, Y, Z, Ar and $R^2$ are as defined in claim 1.

3. A compound according to claim 2 wherein Y is a bond and $R^2$ is hydrocarbon of up to 6 carbon atoms, optionally bearing up to 3 fluorine or chlorine substituents, or is optionally-substituted 5- or 6-membered heteroaryl.

4. A compound according to claim 2 wherein Y is O and $R^2$ represents alkyl, alkenyl, cycloalkyl or cycloalkylalkyl of up to 6 carbon atoms which is optionally substituted with up to 3 fluorine atoms.

5. A compound according to claim 2 wherein Y is NH or NMe and $R^2$ represents alkyl, alkenyl, cycloalkyl or cycloalkylalkyl of up to 6 carbon atoms which is optionally substituted with up to 3 fluorine atoms.

6. A compound according to claim 2 wherein Y represents $NR^3$ and $R^2$ and $R^3$ complete a heterocyclic ring.

7. A compound according to claim 1 according to formula V:

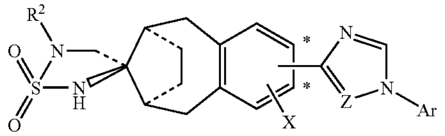

V or a pharmaceutically acceptable salt thereof, where X, Z, Ar and $R^2$ are as defined in claim 1, with the proviso that when X is H, $R^2$ is not 2,2,2-trifluoroethyl.

8. A compound according to claim 7 wherein $R^2$ represents H or a hydrocarbon group of 1-10 carbon atoms which is optionally substituted with up to 3 halogen atoms or with CN or $C_{1-4}$alkoxy.

9. A compound according to claim 1 wherein X is H.

10. A compound according to claim 1 wherein Ar is selected from phenyl, monohalophenyl dihalophenyl, trihalophenyl, cyanophenyl, methylphenyl, methoxyphenyl, trifluoromethyiphenyl, trifluoromethoxyphenyl, pyridyl, monohalopyridyl and trifluoromethylpyridyl, wherein "halo" refers to fluoro or chloro.

11. A pharmaceutical composition comprising a compound according to claim 1 and a pharmaceutically acceptable carrier.

12. A method of treatment of a subject suffering from or prone to Alzheimer's disease which comprises administering to that subject an effective amount of a compound according to claim 1.

* * * * *